(12) United States Patent
Miller et al.

(10) Patent No.: US 8,292,963 B2
(45) Date of Patent: Oct. 23, 2012

(54) EXPANDABLE IMPLANT FOR SUPPORTING SKELETAL STRUCTURES

(75) Inventors: Keith E Miller, Germantown, TN (US); Jonathan M Dewey, Raleigh, NC (US); Dennis A Harrison, II, Atoka, TN (US); Thomas E Drochner, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 363 days.

(21) Appl. No.: 12/428,988

(22) Filed: Apr. 23, 2009

(65) Prior Publication Data

US 2010/0274357 A1 Oct. 28, 2010

(51) Int. Cl.
*A61F 2/44* (2006.01)
*A61B 17/70* (2006.01)

(52) U.S. Cl. ............... 623/17.16; 623/17.15; 623/17.11; 606/246; 606/249; 606/252

(58) Field of Classification Search ............... 623/17, 623/11, 17.15, 17.16; 606/246–279, 63; 285/913
See application file for complete search history.

(56) References Cited

U.S. PATENT DOCUMENTS

| | | | |
|---|---|---|---|
| 1,486,723 A | 3/1924 | Bernson | |
| 4,657,550 A | 4/1987 | Daher | |
| 5,336,223 A | 8/1994 | Rogers | |
| 5,571,192 A | 11/1996 | Schonhoffer | |
| 5,702,453 A | 12/1997 | Rabbe et al. | |
| 5,989,290 A | 11/1999 | Biedermann et al. | |
| 6,015,436 A | 1/2000 | Schonhoffer | |
| 6,190,414 B1 | 2/2001 | Young et al. | |
| 6,660,038 B2 | 12/2003 | Boyer et al. | |
| 6,730,088 B2 | 5/2004 | Yeh | |
| 6,752,832 B2 | 6/2004 | Neumann | |
| 7,575,601 B2* | 8/2009 | Dickson | 623/17.15 |
| 7,879,096 B2* | 2/2011 | Dickson et al. | 623/17.11 |
| 2004/0172129 A1 | 9/2004 | Schafer et al. | |
| 2004/0186569 A1 | 9/2004 | Berry | |
| 2006/0100710 A1 | 5/2006 | Gutlin et al. | |
| 2006/0241762 A1 | 10/2006 | Kraus | |
| 2006/0241770 A1 | 10/2006 | Rhoda et al. | |
| 2007/0028710 A1 | 2/2007 | Kraus et al. | |
| 2007/0255407 A1* | 11/2007 | Castleman et al. | 623/17.11 |
| 2007/0255408 A1* | 11/2007 | Castleman et al. | 623/17.11 |
| 2007/0255410 A1* | 11/2007 | Dickson et al. | 623/17.11 |
| 2007/0255421 A1* | 11/2007 | Dickson | 623/23.47 |
| 2010/0179657 A1 | 7/2010 | Greenhalgh et al. | |
| 2010/0268338 A1* | 10/2010 | Melkent et al. | 623/17.11 |
| 2010/0280614 A1* | 11/2010 | Castleman et al. | 623/17.11 |
| 2011/0251692 A1* | 10/2011 | McLaughlin et al. | 623/17.16 |

FOREIGN PATENT DOCUMENTS

| | | |
|---|---|---|
| DE | 3729600 A1 | 3/1989 |
| DE | 3729600 C2 | 9/1989 |
| DE | 4109941 A1 | 10/1992 |
| DE | 10127924 C1 | 12/2002 |
| EP | 567424 A1 | 10/1993 |
| EP | 567424 B1 | 7/1998 |
| WO | 9525486 A1 | 9/1995 |
| WO | 2004096103 A1 | 11/2004 |
| WO | WO 2008033457 A2 * | 3/2008 |

* cited by examiner

*Primary Examiner* — David Isabella
*Assistant Examiner* — Jacqueline Woznicki

(57) ABSTRACT

Embodiments of the invention include expandable, implantable devices and methods. Devices expand linearly to provide secure fixation between or among anatomical structures. The expanded height of some embodiments is greater that twice the unexpanded height of the device. In some embodiments, an implant replaces one or more vertebral bodies of the spine.

17 Claims, 9 Drawing Sheets

EXPANDABLE IMPLANT FOR SUPPORTING SKELETAL STRUCTURES

FIELD OF THE INVENTION

The present invention relates generally to the field of replacing portions of the human structural anatomy with medical implants, and more particularly relates to an expandable implant and method for replacing skeletal structures such as one or more vertebrae or long bones or portions thereof.

BACKGROUND

It is sometimes necessary to remove one or more vertebrae, or a portion of the vertebrae, from the human spine in response to various pathologies. For example, one or more of the vertebrae may become damaged as a result of tumor growth, or may become damaged by a traumatic or other event. Removal, or excision, of a vertebra may be referred to as a vertebrectomy. Excision of a generally anterior portion, or vertebral body, of the vertebra may be referred to as a corpectomy. An implant is usually placed between the remaining vertebrae to provide structural support for the spine as a part of a corpectomy. FIG. 1 illustrates four vertebrae, $V_1$-$V_4$ of a typical lumbar spine and three spinal discs, $D_1$-$D_3$. As illustrated, $V_3$ is a damaged vertebra and all or a part of $V_3$ could be removed to help stabilize the spine. If removed along with spinal discs $D_2$ and $D_3$, an implant may be placed between vertebrae $V_2$ and $V_4$. Most commonly, the implant inserted between the vertebrae is designed to facilitate fusion between remaining vertebrae. Sometimes the implant is designed to replace the function of the excised vertebra and discs. All or part of more than one vertebra may be damaged and require removal and replacement in some circumstances. It may also be clinically appropriate in some circumstances to remove only one or a part of one of the discs, $D_1$-$D_3$ for example, and replace the disc or a portion of the disc with an expandable implant in a fusion procedure.

Many implants are known in the art for use in a corpectomy or fusion procedure. One class of implants is sized to directly replace the vertebra or vertebrae that are being replaced. Another class of implants is inserted into the human body in a collapsed state and then expanded once properly positioned. Expandable implants may assist with restoring proper loading to the anatomy and achieving more secure fixation of the implant. Expandable implants may be advantageous because they allow for a smaller incision when properly positioning an implant. Implants that expand from a relatively small height to a relatively tall height while providing good structural strength may be more particularly advantageous to minimize incision size. Implants that included insertion and expansion mechanisms that are narrowly configured may also provide clinical advantages. Effective implants should also include a mechanism for securely locking in desired positions, and in some situations, be capable of collapsing. Implants with openings at or near their ends may also be advantageous in some embodiments because they allow for vascularization and bone growth into or through the implant.

Expandable implants may also be useful in replacing long bones or portions of appendages such as the legs and arms, or a rib or other bone that is generally longer than it is wide. Examples include, but are not limited to, a femur, tibia, fibula, humerus, radius, ulna, phalanges, clavicle, and any of the ribs.

SUMMARY

One embodiment of the invention is an expandable medical implant for supporting skeletal structures. The expandable medical implant may include a base with a first end, a second end, and a cannula extending between the first and second ends along a length of the base. The expandable medical implant may also include a first post having a proximal end that travels within the cannula and a distal end that extends beyond the first end of the base, and a second post having a proximal end that travels within the cannula and a distal end that extends beyond the second end of the base. The proximal end of the first post of some embodiments is configured to interdigitate with the proximal end of the second post within the cannula along at least a portion of the length of the base.

An embodiment of the invention is a method of spacing apart vertebral bodies. The method embodiment includes providing an expandable medical implant. The expandable medical implant may have a base with a first end, a second end, and a cannula extending between the first and second ends along a length of the base. The provided expandable medical implant may also include a first post having a proximal end that travels within the cannula and a distal end that extends beyond the first end of the base, and a second post having a proximal end that travels within the cannula and a distal end that extends beyond the second end of the base. The provided expandable medical implant is capable of having a first height between the distal end of the first post and the distal end of the second post, and is capable of expanding to a second height between the distal end of the first post and the distal end of the second post that is greater than the first height. The method includes expanding the first post relative to the base and the second post relative to the base by translating the first and second posts in opposite directions in the cannula so that the medical implant has a second height greater than two times the first height.

Another embodiment of the invention is an expandable medical implant means for spacing apart vertebral structures. The embodiment includes a base having a first end, a second end, and a cannula extending between the first and second ends along a length of the base. The embodiment also includes a first post having a proximal end that travels within the cannula and a distal end that extends beyond the first end of the base, and a second post having a proximal end that travels within the cannula and a distal end that extends beyond the second end of the base. The embodiment additionally includes an expansion means for extending the first post relative to the base and the second post relative to the base in opposite directions in the cannula so that a second height defined by a distance between the distal end of the first post and the distal end of the second post is greater than two times a first height defined by a distance between the distal end of the first post and the distal end of the second post.

DETAILED DESCRIPTION

Figure 1:
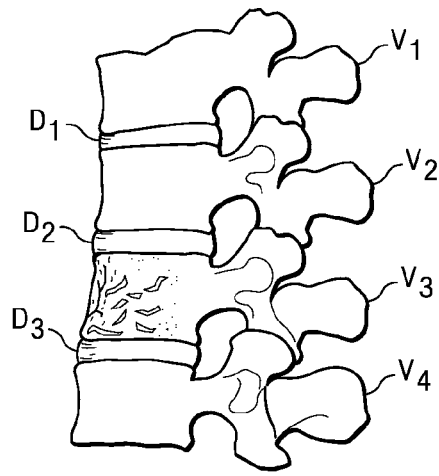
FIG. 1 is an elevation view of a segment of a lumbar spine.

An expandable medical implant for supporting skeletal structures is illustrated in different views and with certain variations in FIGS. 2-12, 18 and 19. The expandable medical implant 1 shown in FIG. 2 includes a base 10, a first post 100 and a second post 200. The base 10 is illustrated with a core 20, a first collar 21, and a second collar 22. The base 10 has a first end 11 and a second end 12. A cannula 13 extends between the first end 11 of the base 10 and second end 12 of the base 10 along a length of the base 10.

Figure 2:
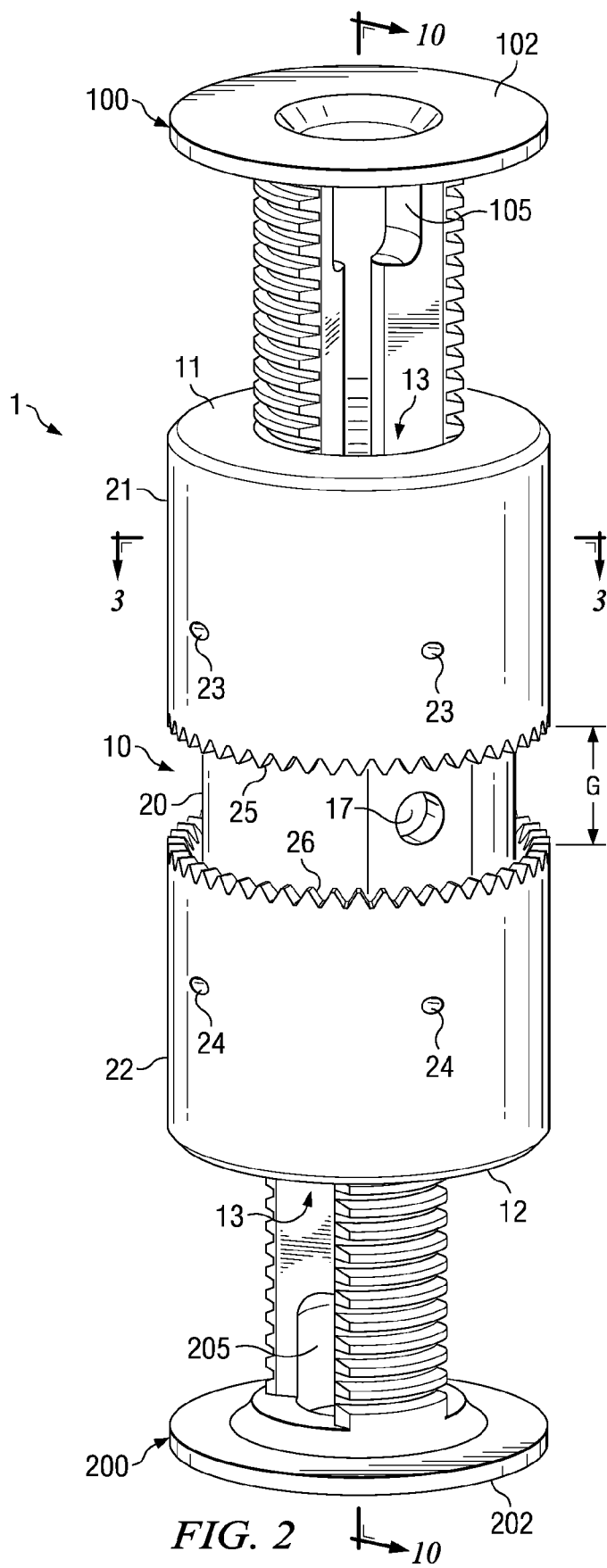
FIG. 2 is a perspective view of an expandable medical implant in a partially expanded state.
Figure 3:
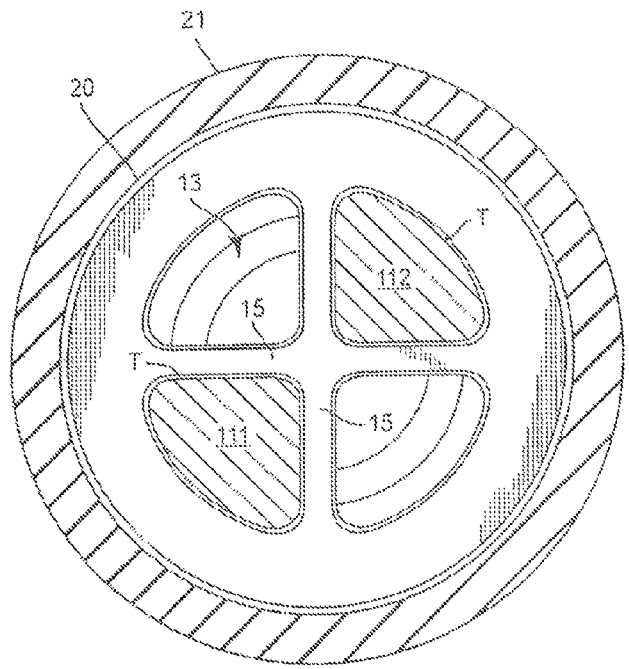
FIG. 3 is a cross-sectional view of the expandable medical implant of FIG. 2.
Figure 5:
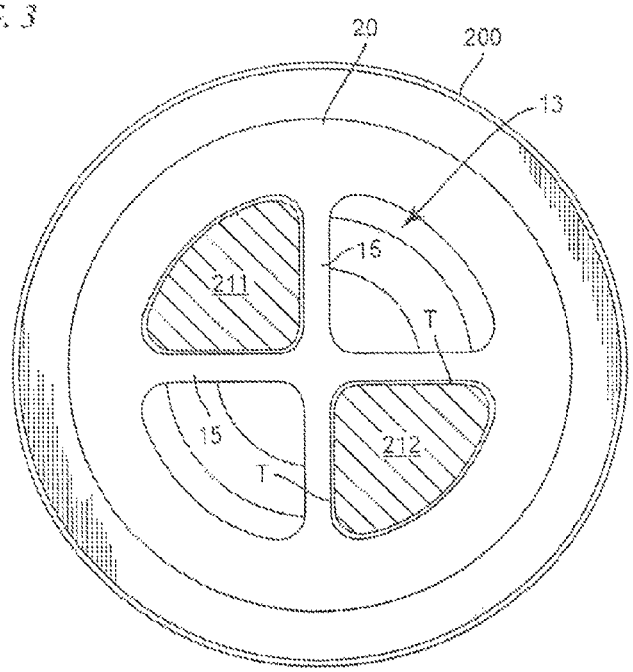
FIG. 5 is a cross-sectional view of the expandable medical implant of FIG. 4.

The core 20 illustrated in FIGS. 2-7 is a cylindrical body. A core of other embodiments could have a cross-sectional shape other than round. For example, the core could be oval, triangular, rectangular, square, an other polygonal or curved shape, or a combination of the shapes noted or other functional shapes. As seen in FIGS. 3-7, the core 20 of the base 10 includes a separator 15 dividing a cross-section of the base 10 such that one or more portions of the first post 100 are divided from one or more portions of the second post 200. In the illustrated embodiment, the separator 15 divides the cross-section of the base 10 into substantially quarter sections. Division into quarter sections may be advantageous in some embodiments because it allows for each of the first post 100 and the second post 200 to have a pair of symmetrical legs occupying opposite quarters of the base. The symmetrical legs are well-positioned to receive loads applied to the posts 100, 200 without particular eccentricities being induced in the materials of the posts 100, 200. Additionally, the configuration provides relatively large amounts of material in each leg that are near the periphery of each of the posts 100, 200. Materials near the peripheries contribute to the ability of the posts 100, 200 to resist loading as columns. In other embodiments, a cross-section of the base 10 may be divided into only two sections so that each post may include a maximum amount of material in a single element. Such an arrangement would minimize the amount of cross-sectional area occupied by a separator and therefore would allow for each post to be as large as possible in cross-section. In still other embodiments, the number of legs of each post may be increase to better distribute the load carried by the posts around a periphery of the base 10, and as noted above, reduce eccentricities, and therefore loads, in the materials of the posts. In addition to approximate wedge sections of a circle as depicted in FIGS. 3 and 5, legs of the posts may be of any functional shape, and the separator 15 may be configured to intervene between all or part of the posts. For example, and without limitation, legs of the posts may be formed with a tongue on one leg or post and a groove on the other leg or post, or the posts may be formed with male and female dovetail connections along their lengths that allow the posts to interconnect.

In some embodiments, the separator may not extend fully across an interior of the base 10, but may merely be a portion of the separator 15 closest to a wall of the base 10. These embodiments may include components that fit between portions of two or more posts, or the components may fit in one or more notches along a side of one or more posts to guide the posts relative to the base.

In some embodiments, the separator 15 is in close tolerance with one or both of the posts 100, 200 to stabilize the posts 100, 200 relative to the base 10. A tolerance "T" is noted in FIGS. 3 and 5. This close tolerance may provide one or both of guidance in dynamic operation of the posts 100, 200 and lateral or other structural stability to the posts 100, 200 in the cannula 13 of the base 10. For example, and without limitation, the separator 15 may be sized to provide gaps or tolerances from 0.02 mm and 1 mm between the posts 100, 200 and the separator 15. Tolerances may be specified between the posts 100, 200 and the separator 15, between portions of the posts 100, 200, or between the posts 100, 200 and other components of the device in various embodiments.

Figure 7:
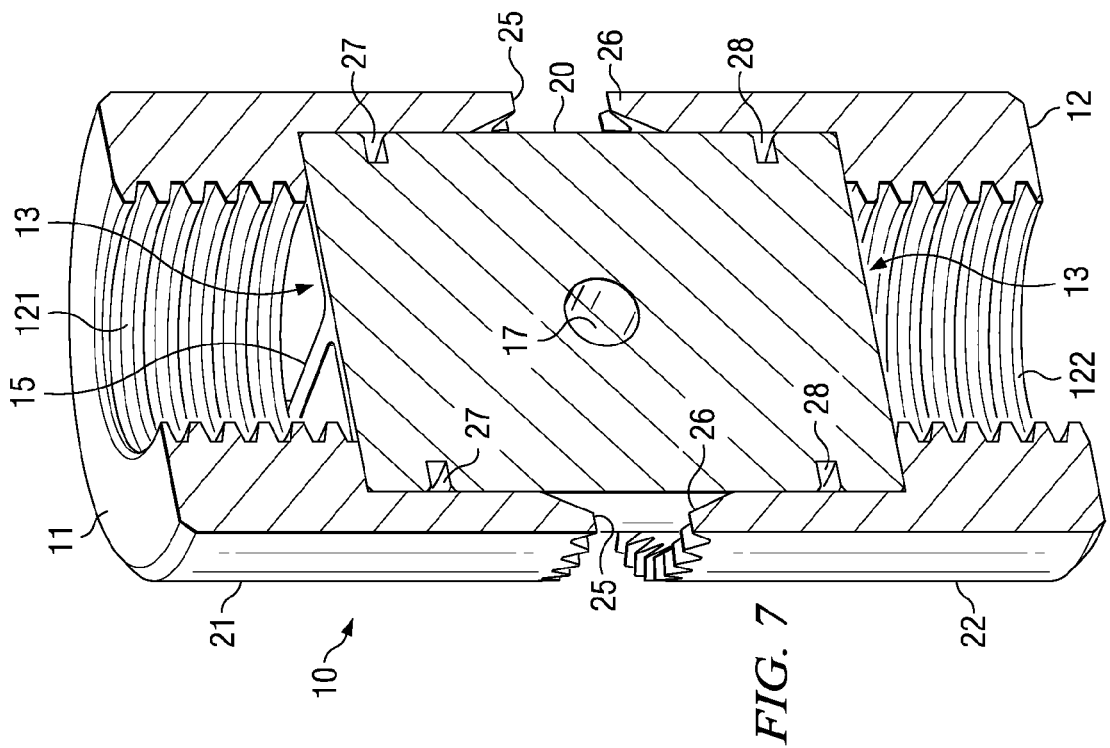
FIG. 7 is cross-sectional view of a perspective view of the expandable medical implant of FIG. 2 with some components removed for illustrative purposes.

The base 10 shown in FIGS. 2, 4, 6, and 7 has an opening 17 for receiving an actuating instrument. In some embodiments, the opening 17 includes threads for receiving threads from a portion of the actuating instrument. As illustrated, the opening 17 is a single hole. A single hole opening would function, with the actuating instrument of FIGS. 13 and 14. However, in other embodiments, the opening 17 may include two or more holes. For example, an opening for receiving the actuating instrument depicted in FIGS. 15-17 includes a set of three holes. The base 10 may include holes in one or more sides of the base 10. As shown in FIG. 7, the opening 17 passes through the center of the base 10 to provide the opening 17 in opposite sides of the base 10. In other embodiments, the base 10 may include a protrusion rather than a hole. An instrument may fit with the protrusion to align an actuating instrument on the expandable medical implant 1.

Figure 4:
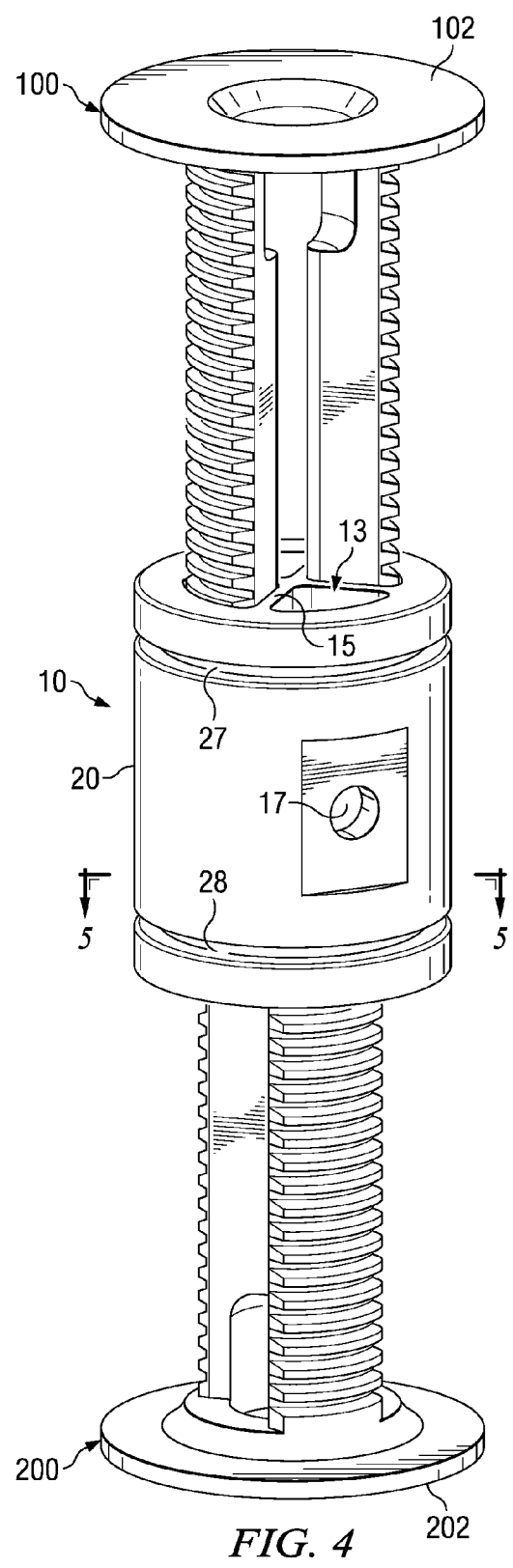
FIG. 4 is a perspective view of the expandable medical implant of FIG. 2 with some components removed for illustrative purposes.
Figure 6:
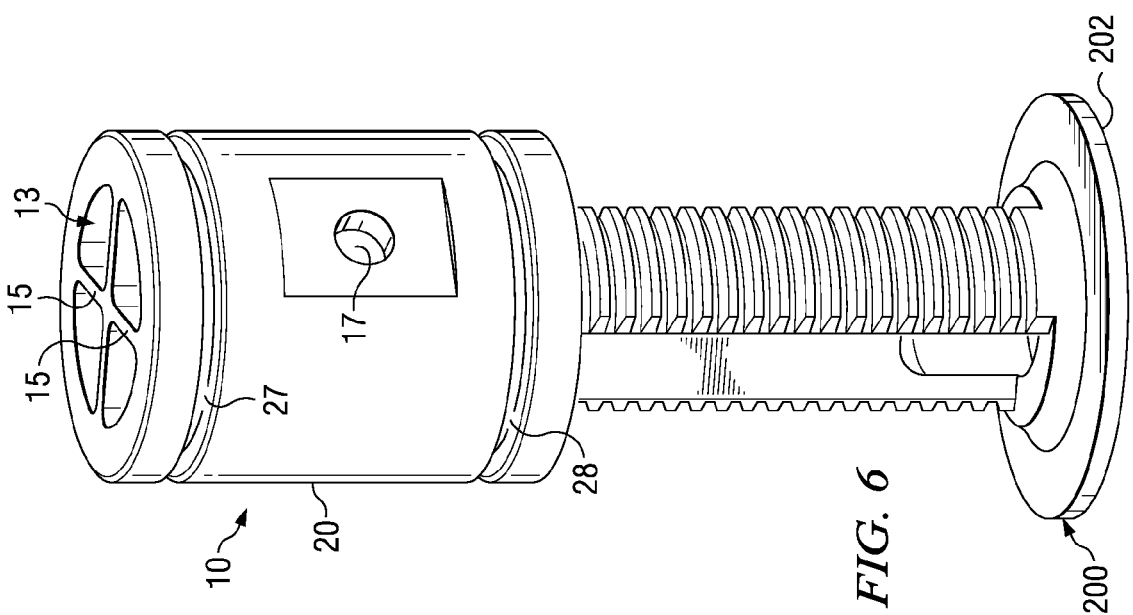
FIG. 6 is a perspective view of the expandable medical implant of FIG. 2 with some components removed for illustrative purposes.
Figure 8:
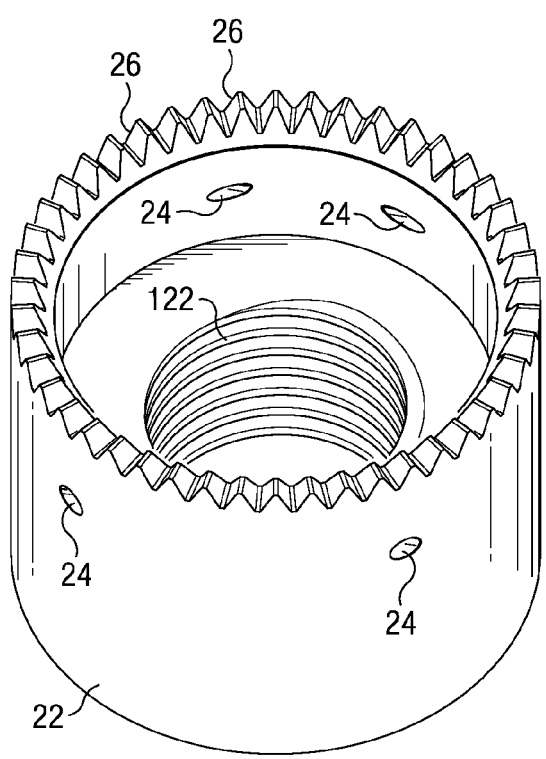
FIG. 8 is a perspective view of an embodiment of a collar of some embodiments of the invention.

In some embodiments, the base 10 includes the first collar 21 and the second collar 22. The first collar 21 and the second collar 22 in the illustrated embodiments are configured to regulate motion of the first post 100 and the second post 200 respectively along the length of the base 10. The first collar 21 of the illustrated embodiment is coupled to the core 20 of the base 10 by pins (not shown) that are fixed in holes 23 (FIGS. 2 and 10) and pass through a groove 27 (FIGS. 4, 6, and 7). The first collar 21 may be coupled to the core 20 by any effective device, including but not limited to, through retaining rings, set screws, or staking in the groove 27. The first collar 21 is allowed to rotate about the core 20 as the pins travel in the groove 27. The first collar 21 illustrated includes teeth 25 around its perimeter that are configured to receive an instrument for rotating the first collar 21 relative to a portion of the base 10, such as the core 20. For example and without limitation, the teeth 25 may receive one of the actuating instruments shown in FIGS. 13-17.

The second collar 22 of the illustrated embodiment is coupled to the core 20 of the base 10 by pins (not shown) that are fixed in holes 24 (FIGS. 2, 8, and 10) and pass through a groove 28 (FIGS. 4, 6, and 7). The second collar 22 is allowed to rotate about the core 20 as the pins travel in the groove 28. The second collar 22 may be coupled to the core 20 by any effective device, including but not limited to, through retaining rings, set screws, or staking in the groove 28. The second collar 22 illustrated includes teeth 26 around its perimeter that are configured to receive an instrument for rotating the second collar 22 relative to a portion of the base 10, such as the core 20. For example and without limitation, the teeth 26 may receive one of the actuating instruments shown in FIGS. 13-17.

For the illustrated embodiments, the first collar 21 and the second collar 22 may be turned simultaneously with an instrument. For example, the instrument of FIGS. 13 and 14 or the instrument of FIGS. 15-17 may be connected to the core 20 to simultaneously turn the first collar 21 and the second collar 22. In the illustrated configuration, the first collar 21 and the second collar 22 would be turned in opposite directions by either of the instruments of FIGS. 13-17. However, because the first collar 21 and the second collar 22 have identical thread patterns, but are turned proximal end to proximal end, rotating them in opposite directions results in the first post 100 and the second post 200 moving together simultaneously and moving apart simultaneously. Any other operable combination of thread patterns and gears is also contemplated under embodiments of the invention. For example and without limitation, an actuating instrument may only have two intermeshing gears so that collars above and below would be moved in the same, rather than opposite, rotational directions. This configuration could be operable in conjunction with collars that have opposite thread patterns, for example, one with right-hand threads and one with left-hand threads.

Embodiments of the first post 100 and the second post 200 are illustrated in FIGS. 2, 4, 9, and 10. The first post 100 has a proximal end 101 and a distal end 102. The proximal end 101 travels within the cannula 13, and the distal end 102 extends beyond the first end 11 of the base 10. As illustrated, the first collar 21 is coupled to the first post 100 by threads 121 (FIGS. 7 and 10) such that motion of the first post 100 along the length of the base 10 is induced by rotation of the first collar 21.

The second post 200 has a proximal end 201 and a distal end 202. The proximal end 201 travels within the cannula 13, and the distal end 202 extends beyond the second end 12 of the base 10. As illustrated, the second collar 22 is coupled to the second post 200 by threads 122 (FIGS. 7, 8, and 10) such that motion of the second post 200 along the length of the base 10 is induced by rotation of the second collar 22.

The separator 15 of some embodiments also contributes toward preventing the threads 121, 122 of the collars from disengaging with the respective posts 100, 200. Turning forces that create work along the threads may generate resulting forces that tend to push the posts 100, 200 toward the center of the base 10 as forces are applied to the threads. The separator 15 may contact generally opposite sides of the respective posts 100, 200 to counteract the resulting forces and allow the threads 121, 122 of the collars to remain engaged with the posts 100, 200.

Figure 9:
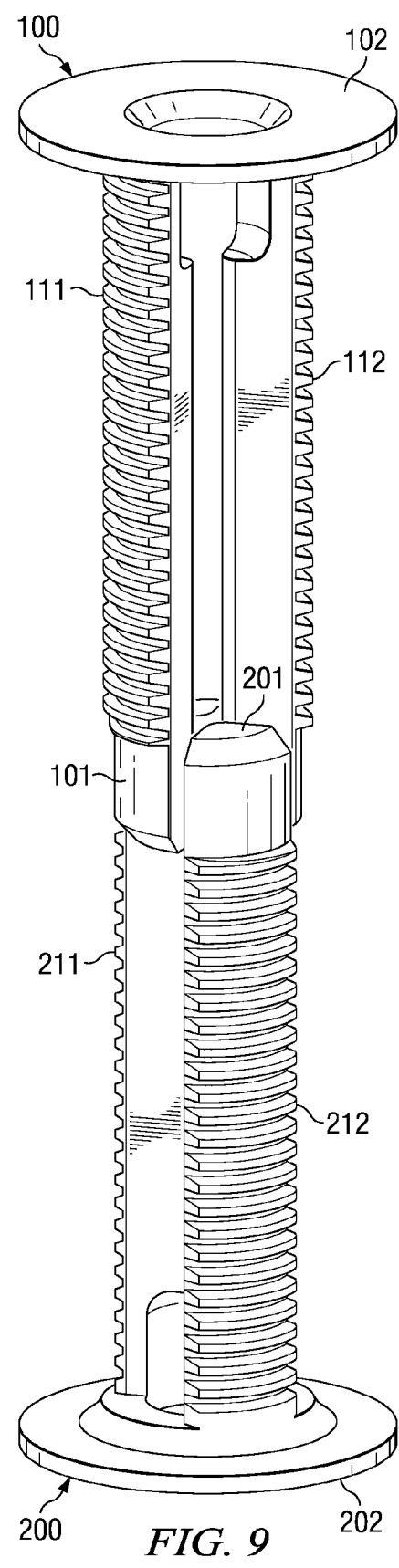
FIG. 9 is a perspective view of an embodiment of posts of some embodiments of the invention.
Figure 10:
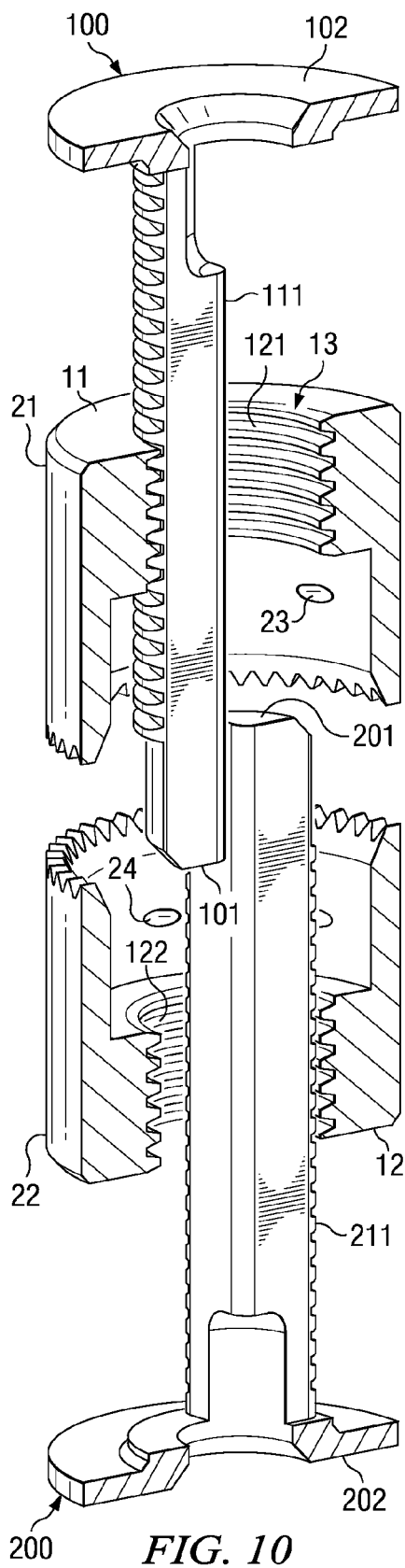
FIG. 10 is a cross-sectional view of a perspective view of the expandable medical implant of FIG. 2 with some components removed for illustrative purposes.

FIGS. 9 and 10 illustrate the proximal end 101 of the first post 100 interdigitated with the proximal end 201 of the second post 200. The proximal end 101 of the first post 100 interdigitates with the proximal end 201 of the second post 200 within the cannula 13 along at least a portion of the length of the base 10 in some embodiments. The term interdigitate and variations of the term used herein refer to components that mesh together, intermingle, or overlap along their lengths. Components are considered to be configured to interdigitate when the components have a shape that will allow portions of the components to pass by one another and occupy a common cross-sectional plane along a length of the components. As applied to the embodiment illustrated in FIGS. 9 and 10, the first post 100 is configured to interdigitate with the second post 200 because legs 111, 112 of the first post 100 are shaped to fit in a common cross-sectional plane with legs 211, 212 of the second post 200 along a length of the first and second posts 100, 200. More particularly for the illustrated embodiment, the first post 100 and the second post 200 each include two opposing, interdigitating legs 111, 112, and 211, 212. Each illustrated leg 111, 112, 211, 212 is located substantially at a quarter point of a cross-section of the base 10. In other embodiments, there may only be two legs such that each post 100, 200 includes a maximum amount of material to the exclusion of separator components, as noted above. Some embodiments of the posts may include more than two pairs of interdigitating legs that distribute the load carried by the posts around a periphery of the base to reduce loading eccentricities, and therefore stresses in the materials of the posts.

One or both distal ends 102, 202 of the posts 100, 200 may include end pieces or shoes that connect with respective adjacent vertebral bodies. The shoes may include features that add an angled configuration to the distal ends 102, 202 so that an implant will match or alter a lordotic, kyphotic spinal curvature or a curvature resulting from scoliosis. Alternatively or in addition, the shoes may include features that enhance connection to a vertebra. For example and without limitation, the shoes may include teeth, spikes, fasteners, openings, knurling, roughened surfaces, or any surface treatments or additional materials that are effective to enhance connection to a vertebra.

Figure 11:
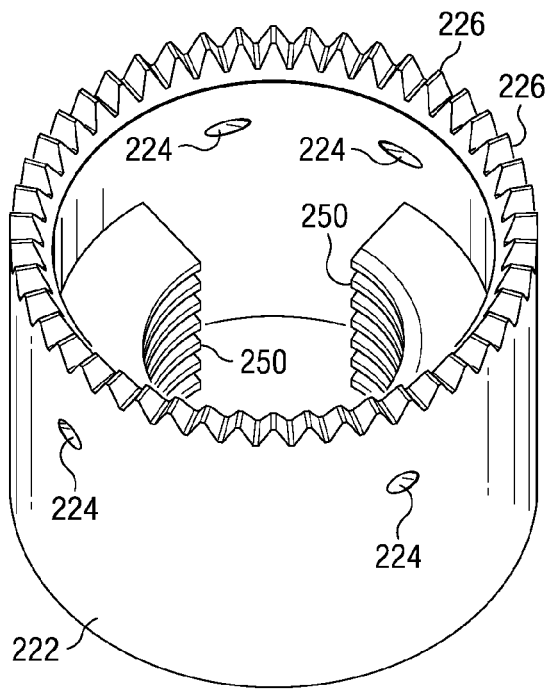
FIG. 11 is a perspective view of an embodiment of a collar of some embodiments of the invention.
Figure 12:
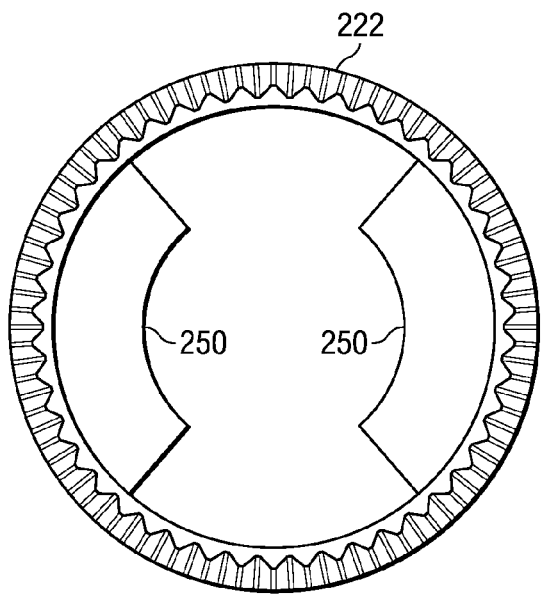
FIG. 12 is a plan view of the collar of FIG. 11.

Another embodiment of a collar is illustrated in FIGS. 11 and 12. A collar 222 is shown that may be substituted on either or both ends of the core 20. The collar 222 may by coupled to the core 20 of the base 10 by pins (not shown) that are fixed in holes 224 and pass through either of the grooves 27, 28 (FIGS. 4, 6, and 7). The collar 222 is allowed to rotate about the core 20 as the pins travel in the grooves 27, 28. The collar 222 may be coupled to the core 20 by any effective device, including but not limited to, through retaining rings, set screws, or staking in the grooves 27, 28. The collar 222 illustrated includes teeth 226 around its perimeter that are configured to receive an instrument for rotating the collar 222 relative to a portion of the base 10. For example and without limitation, the teeth 226 may receive one of the actuating instruments shown in FIGS. 13-17.

The first post 100 with distal end 102 and proximal end 101 that travels within the cannula 13 may be configured to couple with the collar 222 through engagement mechanisms 250. The engagement mechanisms 250 are disposed around one or more segments of an interior diameter of the collar 222. When the collar 222 is in a first rotational position where the engagement mechanisms 250 do not interact with threads on the first post 100, movement of the first post 100 along the base 10 is allowed. When the collar 222 is in a second rotational position where the engagement mechanisms 250 couple with threads on the first post 100, movement of the first post 100 along the base 10 is restricted. For the illustrated collar 222, the rotational movement between the first rotational position and the second rotational position is approximately 90 degrees. The collar 222 and engagement mechanism 250 may be similarly employed at the second end 12 of the base 10 in combination with the second post 200. In other embodiments where one or both of the threads of the post or the segments of engagement mechanisms 250 are sized differently, the rotational movement between the first and second rotational positions would be changed proportionally. The engagement mechanisms 250 of the illustrated embodiment are threads that engage with threads of the respective posts. In other embodiments, expansion and collapse of the medical implant may be regulated by ratchet teeth or any other functional mechanism. Embodiments of the collar 222 with appropriate engagement mechanisms 250 would be equally effective with these other mechanisms and are contemplated under embodiments of the invention.

Figure 18:
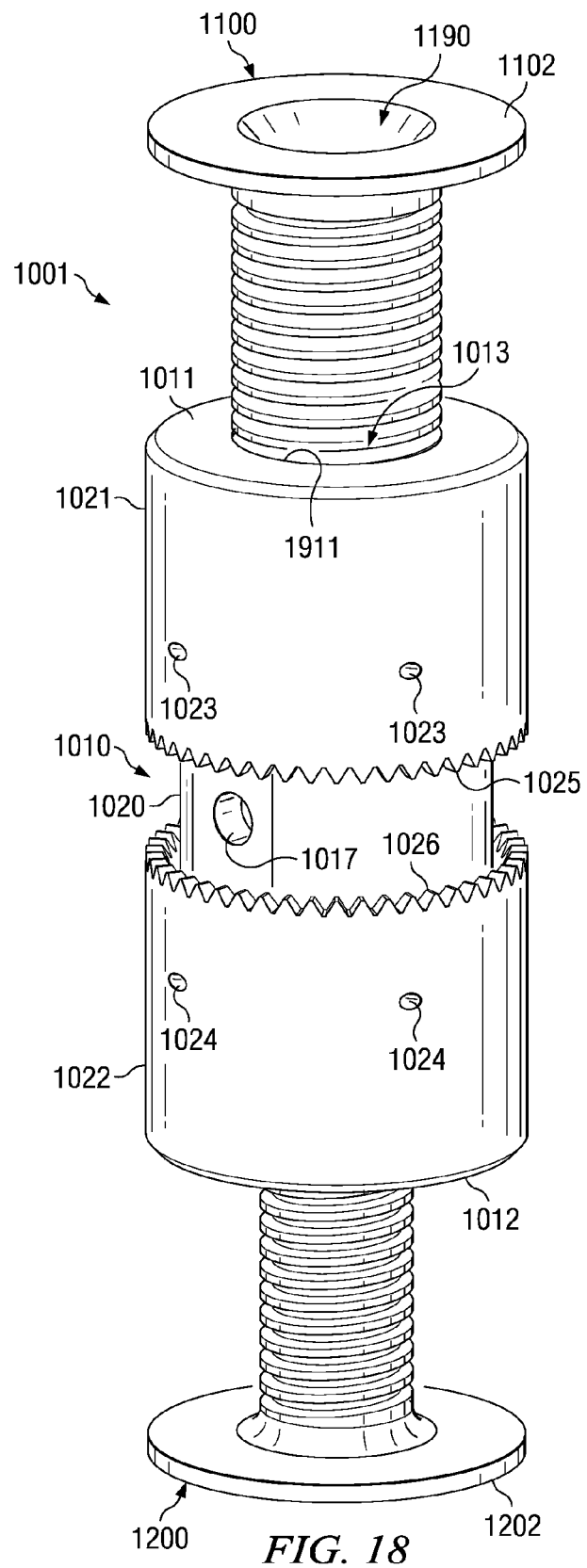
FIG. 18 is a perspective view of an expandable medical implant in a partially expanded state.
Figure 19:
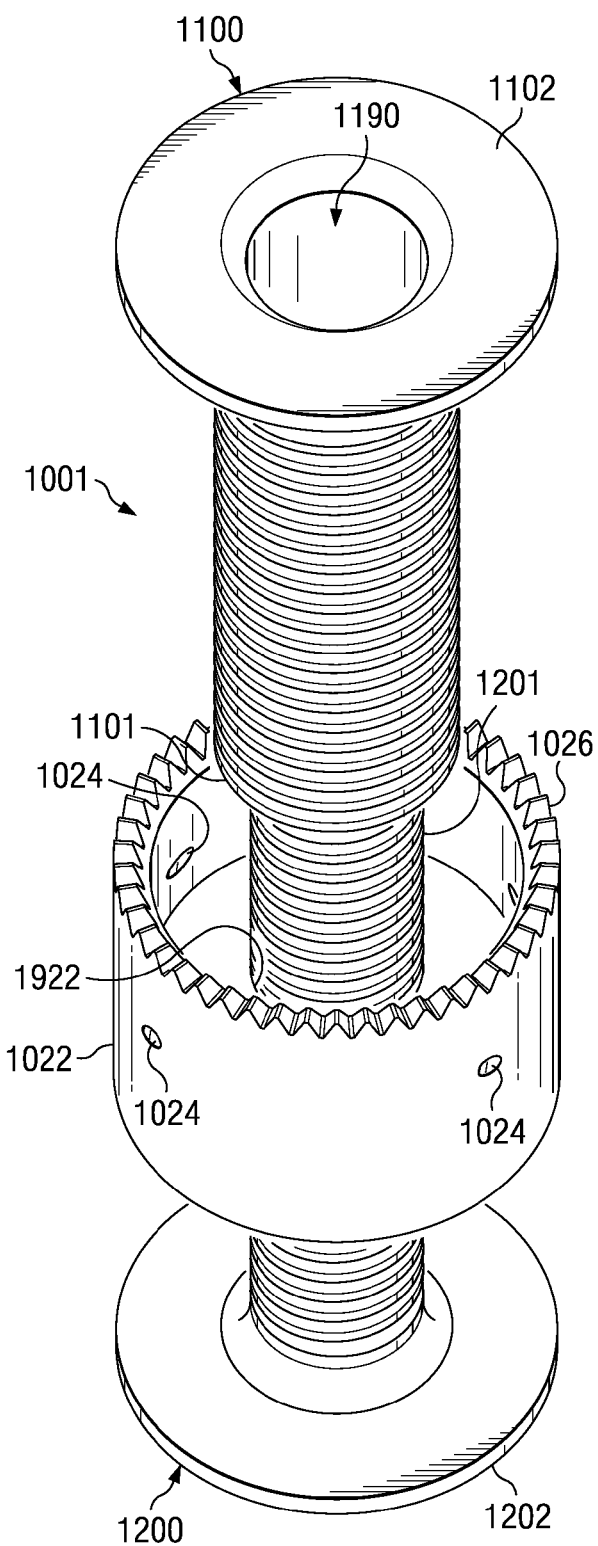
FIG. 19 is a perspective view of the expandable medical implant of FIG. 18 with some components removed for illustrative purposes.

Another embodiment of the expandable medical implant is illustrated in FIGS. 18 and 19. The expandable medical implant 1001 shown includes a base 1010, a first post 1100 and a second post 1200. The base 1010 is illustrated with a core 1020, a first collar 1021, and a second collar 1022. The base 1010 has a first end 1011 and a second end 1012. The illustrated core 1020 is generally cylindrical and includes openings for one or both of the first and second posts 1100, 1200 to pass through the core 1020. A cannula 1013 extends between the first end 1011 of the base 1010 and second end 1012 of the base 1010 along a length of the base 1010. In FIG. 18, the cannula 1013 is occupied by the first and second posts 1100, 1200. The base 1010 shown has an opening 1017 for receiving an actuating instrument. Configurations and functions of the opening 1017 and related structures are essentially similar to those describe in association with the opening 17 above.

The first collar 1021 and the second collar 1022 in the illustrated embodiment are configured to regulate motion of the first post 1100 and the second post 1200 respectively along the length of the base 1010. The first collar 1021 is coupled to the core 1020 of the base 1010 by pins (not shown) that are fixed in holes 1023 (FIG. 18) and pass through a groove (not shown) in the core 1020. The first collar 1021 is allowed to rotate about the core 1020 as the pins travel in the groove. The first collar 1021 may be coupled to the core 1020 by any effective device, including but not limited to, through retaining rings, set screws, or staking in the groove. The first collar 1021 illustrated includes teeth 1025 around its perimeter that are configured to receive an instrument for rotating the first collar 1021 relative to a portion of the base 1010, such as the core 1020. For example and without limitation, the teeth 1025 may receive one of the actuating instruments shown in FIGS. 13-17.

The second collar 1022 is coupled to the core 1020 of the base 1010 by pins (not shown) that are fixed in holes 1024 (FIGS. 18 and 19) and pass through a groove (not shown) in the core 1020. The second collar 1022 is allowed to rotate about the core 1020 as the pins travel in the groove. The second collar 1022 may be coupled to the core 1020 by any effective device, including but not limited to, through retaining rings, set screws, or staking in the groove. The second collar 1022 illustrated includes teeth 1026 around its perimeter that are configured to receive an instrument for rotating the second collar 1022 relative to a portion of the base 1010, such as the core 1020. For example and without limitation, the teeth 1026 may receive one of the actuating instruments shown in FIGS. 13-17. Operation of the first and second collars 1021 and 1022 with actuating instruments is essentially similar to the operation of the first and second collars 21, 22 described above.

Embodiments of the first post 1100 and the second post 1200 are illustrated in FIGS. 18 and 19. The first post 1100 has a proximal end 1101 and a distal end 1102. The proximal end 1101 travels within the cannula 1013, and the distal end 1102 extends beyond the first end 1011 of the base 1010. As illustrated, the first collar 1021 is coupled to the first post 1100 by threads such that motion of the first post 1100 along the length of the base 1010 is induced by rotation of the first collar 1021.

The second post 1200 has a proximal end 1201 and a distal end 1202. The proximal end 1201 travels within the cannula 1013, and the distal end 1202 extends beyond the second end 1012 of the base 1010. As illustrated, the second collar 1022 is coupled to the second post 1200 by threads such that motion of the second post 1200 along the length of the base 1010 is induced by rotation of the second collar 1022. Because the second post 1200 has a smaller diameter than the first post 1100, a threaded opening 1922 (FIG. 19) in the second collar 1022 is smaller than a threaded opening 1911 (FIG. 18) in the first collar 1021. The pitch of the threads of the threaded openings 1911 and 1922 may be the same pitch, or a different pitch. Different pitches may be useful in some embodiments to cause different rates of travel for the first and second posts 1100, 1200 in response to a common actuation. Different rates of travel may also permit greater overall expansion capacity by making a second post longer than a first post, since the longer second post would be able to nest through the center of the first post and extend all the way to a distal end of the first post. The longer second post may be expanded at a faster rate over its entire length and thereby give the implant a greater overall expansion distance.

As shown in FIG. 19, the proximal end 1101 of the first post 1100 is interdigitated with the proximal end 1201 of the second post 1200. As applied to the embodiment illustrated in FIGS. 18 and 19, the first post 1100 is configured to interdigitate with the second post 1200 by receiving the second post 1200 within the inner diameter of the first post 1100. The first and second posts 1100, 1200 of the illustrated embodiment are tubular, round in cross-section, and threaded. However, in other embodiments, the posts may be oval, triangular, rectangular, square, an other polygonal or curved shape, or a combination of the shapes noted or other functional shapes. Various embodiments may or may not have threads, and may alternatively or in addition have ratchetings, notches, or other surfaces that may be engaged or gripped to move or hold the first and second posts.

A central bore 1190 is shown in FIGS. 18 and 19. The central bore 1190 may extend completely or partially through one or both of the first and second posts 1100, 1200. The central bore 1190 may be filled in whole or in part with bone growth promoting substances, such as the substances detailed below. Bone growth promoting substance may be added to the central bore 1190 before implantation, during the expansion process of the implant, after the implant is implanted and fully expanded, or at any combination of the listed times.

Expandable medical implants under some embodiments are means for spacing apart vertebral structures. An expandable medical implant may include a base having a first end, a second end, and a cannula extending between the first and second ends along a length of the base; a first post having a proximal end that travels within the cannula and a distal end that extends beyond the first end of the base; and a second post having a proximal end that travels within the cannula and a distal end that extends beyond the second end of the base. Embodiments of the expandable medical implant may further include an expansion means for extending the first post relative to the base and the second post relative to the base in opposite directions in the cannula so that a second height defined by a distance between the distal end of the first post and the distal end of the second post is greater than two times a first height defined by a distance between the distal end of the first post and the distal end of the second post. In the illustrated embodiments, the first post 100 is a single component and the second post 200 is a single component. Consequently, in order for the expanded second height between the distal ends 102, 202 to be greater than two times the first height, the first post 100 and the second post 200 interdigitate within the base 10. In some embodiments, such as but not limited to the embodiment illustrated in FIGS. 18 and 19, the first and second posts may interdigitate as concentric cylindrical cross-sections that extend from opposite ends of a base.

Figure 13:
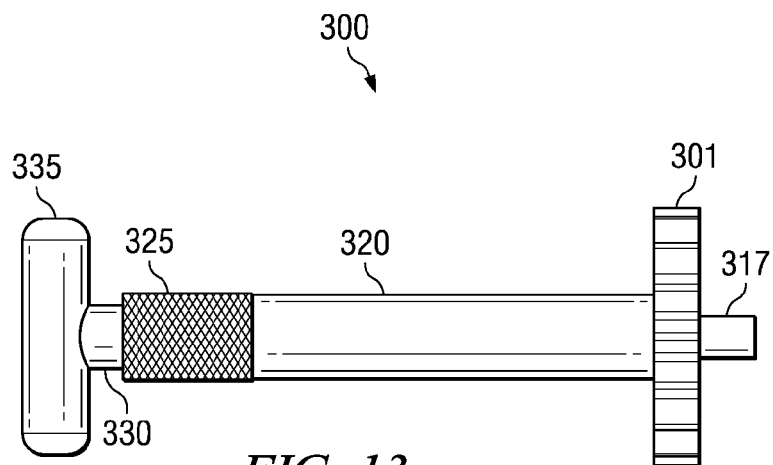
FIG. 13 is an elevation view of an instrument embodiment.
Figure 14:
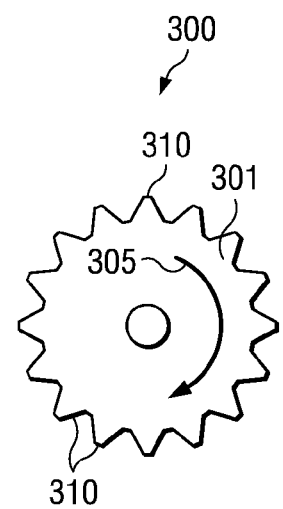
FIG. 14 is an elevation view of an end of the instrument of FIG. 13.

Actuating instruments 300, 400 are illustrated in FIGS. 13-17. The actuating instruments 300, 400 are configured to operate with one or more collars 21, 22, 222, 1021, 1022 of some embodiments to regulate motion of the first post 100, 1100 and the second post 200, 1200 respectively along the length of the base 10. As shown in FIGS. 13 and 14, embodiments of the actuating instrument 300 include a single gear 301 with gear teeth 310 configured to engage with teeth 25, 26, 226, 1025, 1026 of one or more of the collars 21, 22, 222, 1021, 1022. The actuating instrument 300 includes a tube 320 in which a shaft 330 is rotatably coupled. A gripping surface 325 may be applied to an exterior portion of the tube 320. A handle 335 may be included on a proximal end of the shaft 330 for grasping to turn the shaft 330 relative to the tube 320. The shaft 330 is coupled to the gear 301. A tab 317 may be rotatably coupled in the opening 17 to secure the actuating instrument 300 to the base 10 while allowing the gear 301 to turn relative to the base 10. The tab 317 of some embodiments may include a threaded portion to connect to a threaded area of the opening 17, where the threaded portion rotates relative to the shaft 330. In other embodiments, the tab 317 may include devices to expand or otherwise change shape to rotatably or fixedly connect with the opening 17 or other portion of the base 10. As shown by arrow 305 in FIG. 14, rotation of the gear 301 results in motion relative to the gear 301 at the top of the gear in a first direction and motion at the bottom of the gear in a second direction opposite from the first direction. This configuration may be useful with a device such as expandable medical implant 1 where this action results in counter-rotation of first collar 21 and second collar 22 and simultaneous movement of posts 100, 200 toward a collapsed or expanded state. The diameter of the gear 301 may be altered in various embodiments to fit with implants with different distances G between gears (FIG. 2).

Figure 15:
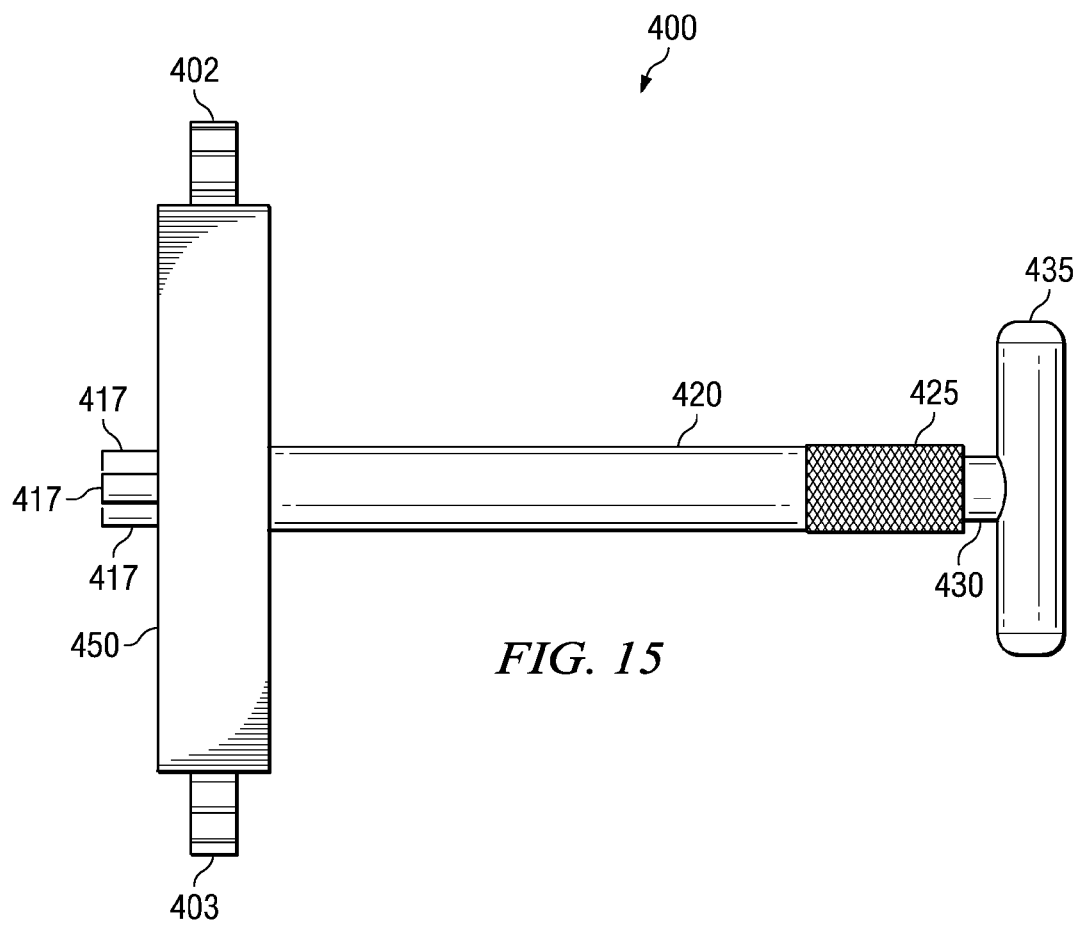
FIG. 15 is an elevation view of an instrument embodiment.
Figure 16:
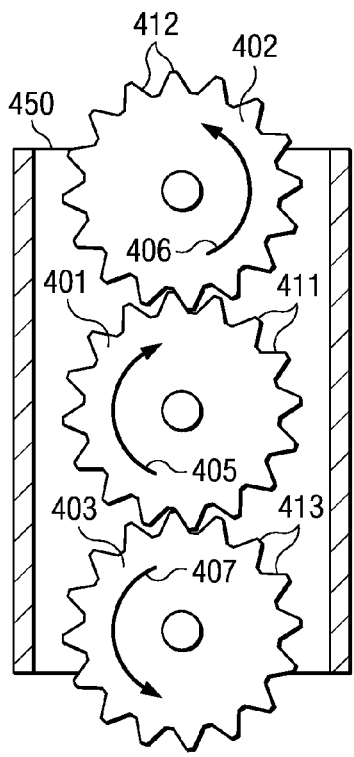
FIG. 16 is an elevation view of an end of the instrument of FIG. 15 with an end portion removed for illustrative purposes.
Figure 17:
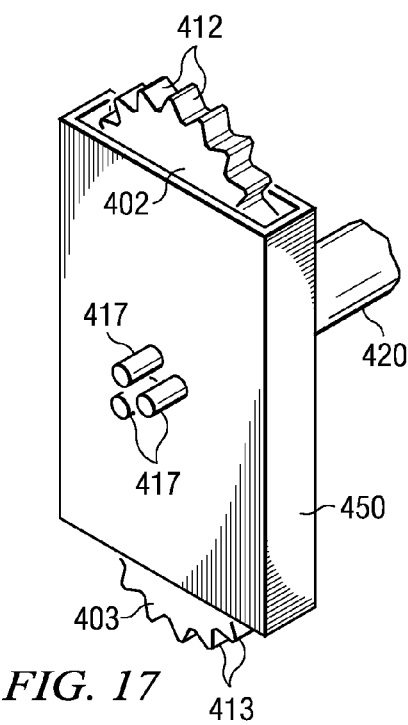
FIG. 17 is a perspective view on an end of the instrument of FIG. 15.

As shown in FIGS. 15-17, embodiments of the actuating instrument 400 include three gears 401, 402, 403 with gear teeth 411, 412, 413. The gear teeth 412, 413 are configured to engage with teeth 25, 26, 226, 1025, 1026 of one or more of the collars 21, 22, 222, 1021, 1022. The actuating instrument 400 includes a tube 420 in which a shaft 430 is rotatably coupled. A gripping surface 425 may be applied to an exterior portion of the tube 420. A housing 450 is coupled to the tube 420 in the embodiment shown. A tab 417 is coupled to the housing 450. A handle 435 may be included on a proximal end of the shaft 430 for grasping to turn the shaft 430 relative to the tube 420. The shaft 430 is coupled to the gear 401. The tab 417 has three prongs in the illustrated embodiment and may be inserted in an opening in a base similar to the base 10 to secure the actuating instrument 400 to the base while allowing the gear 401 to turn relative to the base. The opening in which the actuating instrument 400 is inserted in the illustrated embodiment is similar to some embodiments of the opening 17 but includes holes for at least three prongs. One or more of the prongs of the tab 417 of some embodiments may include a threaded portion to connect to a threaded area of an opening. The tab 417 may include devices to expand, change orientation, or otherwise change shape to connect with a base or another portion of an implant. In FIG. 16, an end portion of the housing 450 is shown removed for illustrative purposes.

As depicted by arrow 405 in FIG. 16, rotation of the gear 401 results in motion relative to the gear 401 at the top of the gear 401 in a first direction and motion at the bottom of the gear 401 in a second direction opposite from the first direction. The gear 401 meshes with and turns a gear 402 at the top of the gear 401 in a rotational direction depicted by arrow 406. The gear 401 meshes with and turns a gear 403 at the bottom of the gear 401 in a rotational direction depicted by arrow 407. This configuration may be useful with a device such as expandable medical implant 1 where this action results in counter-rotation of first collar 21 and second collar 22 and simultaneous movement of posts 100, 200 toward a collapsed or expanded state. The diameter of the gears 401, 402, 403 may be altered in various embodiments to fit with implants with different distances G between gears (FIG. 2) or to generate different amounts of mechanical advantage or relative rate of turning. For example and without limitation, the collars 21, 22, 222, 1021, 1022 may be more narrow top to bottom in some embodiments and create a greater distance G between gears of the collars. Rotation of the handle 435 of the actuating instrument 400 results in an opposite rotation of collars 21, 22, 222, 1021, 1022 compared with a like rotation of the handle 335 of the actuating instrument 300. In still another embodiment, an actuating instrument (not shown) may include two gears so that rotation of the upper and lower parts of the instrument would be in a common direction. Such a rotation may be useful where upper and lower collars of an implant have opposite thread directions or for various other implant embodiments.

An embodiment of the invention is a method of spacing apart vertebral bodies. The method may include providing an expandable medical implant and expanding the implant so that the medical implant has an expanded height greater than two times the height of the implant or a component of the implant in an unexpanded state. For example expandable medical implants of the method may be capable of having a first height between a distal end of a first post and a distal end of a second post, and may be capable of expanding to a second height between the distal end of the first post and the distal end of the second post that is greater than the first height. The method may also include expanding the first post relative to the base and the second post relative to the base by translating the first and second posts in opposite directions in the cannula so that the second height is greater than two times the first height.

Referring to a non-limiting example, the expandable medical implant 1 has a base 10 with a first end 11, a second end 12, and a cannula 13 extending between the first end 11 and the second end 12 along a length of the base 10. The illustrated first post 100 has a proximal end 101 that travels within the cannula 13, and a distal end 102 that extends beyond the first end 11 of the base 10. The illustrated second post 200 has a proximal end 201 that travels within the cannula 13, and a distal end 202 that extends beyond the second end 12 of the base 10. In the example, a first height is defined between the distal end 102 of the first post 100 and the distal end 202 of the second post 200. The expandable medical implant 1 may be capable of expanding to a second height between the distal end 102 of the first post 100 and the distal end 202 of the second post 200 that is greater than the first height. The first post 100 of the illustrated embodiment is a unitary piece that does not telescope, fold out, or expand in any way with additional components beyond its distal end 102. Likewise, the second post 200 of the illustrated embodiment is a unitary piece that does not telescope, fold out, or expand in any way with additional components beyond its distal end 202. The diameters or lateral periphery of the proximal ends 101, 201 of the posts 100, 200 of the illustrated embodiment are approximately equal, thus giving the posts 100, 200 approximately the same structural characteristics and load capacity.

Continuing with the present example, expanding the medical implant 1 includes expanding the first post 100 relative to the base 10 and the second post 200 relative to the base 10. The expansion of the embodiment shown includes translating the first and second posts 100, 200 in opposite directions in the cannula 13 so that the medical implant 1 has a second height that is greater than two times the first height. In some embodiments, the expansion distance may also be defined as expanding to a total height greater than two times the height of the base 10. For the device shown, the first post 100 and the second post 200 are moved relative to the base 10 by rotating the collars 21, 22 that are engaged with threads on the posts 100, 200. In particular, the collars 21, 22 are rotated by inserting a tip of an instrument, such as either of the tabs 317, 417 of the activation instruments 300, 400, into the base 10 and rotating the respective handles 335, 435 of the instruments to turn one or more gears that mesh with the teeth 25, 26 of the collars 21, 22. In other embodiments, either of the collars 21, 22 may be independently turned to selectively control expansion from either end of the base 10.

In an alternate embodiment, an expandable medical implant is expanded by attaching an expansion instrument to a distal end of a first post and a distal end of a second post. The expansion instrument may be of any variety capable of moving the distal ends away from one another. For example and without limitation, expansion instruments with mechanical linkages that react to spreading or compressing proximal components, screw driven devices, ratcheting devices, hydraulic, electrical, or other powered devices may be used to move the distal ends of the posts apart. Method embodiments include operating such an instrument to expand the expandable medical implant. Once expanded, the expandable medical implant may be locked into place by any effective mechanism. Non-limiting examples include locking with a pin, a set screw or other fastener, a locking ring, a clamp, an interference fit, and a collar. A more specific example of a collar is embodied in the collar 222. Method embodiments may further include positioning the collar 222 is in a first rotational position where the engagement mechanisms 250 do not interact with threads on the posts 100, 200 while the posts 100, 200 are translated relative to the base 10. When the posts 100, 200 are moved to an acceptable position, the collar 222 may be moved to a second rotational position where the engagement mechanisms 250 couple with threads on the respective posts 100, 200, thus restricting movement of the posts 100, 200 along the base 10. As illustrated, the rotational movement between the first rotational position and the second rotational position is approximately 90 degrees. In other embodiments where one or both of the threads of the posts 100, 200 or the segments of engagement mechanisms 250 are sized differently, the rotational movement between the first and second rotational positions would be changed proportionally.

Some embodiments may also include supplemental fixation devices as part of the expandable medical implant for further stabilizing the anatomy. For example, and without limitation, rod and screw fixation systems, anterior or lateral plating systems, facet stabilization systems, spinal process stabilization systems, and any devices that supplement stabilization may be used as a part of the expandable medical implant.

In some embodiments, the expandable medical implant may also include a bone growth promoting substance as part of or in combination with the expandable medical implant. All or a portion of the interior and/or periphery of the implant may be packed with a suitable bone growth promoting substance or therapeutic composition. For example, and without limitation, one or both of an end chamber 105, 205 (FIG. 2) may be filled with a bone growth promoting substance such as an osteogenic material to promote bone growth into the respective distal ends 102, 202 of the expandable medical implant 1. In other embodiments, a chamber may be created in a shoe to be placed on the end of a post, or a chamber may extend the entire length of the expandable medical implant that may be filled during or after expansion. The central bore 1190 shown in FIGS. 18 and 19 may be filled in whole or in part with a bone growth promoting substance. Bone growth promoting substances include, without limitation, autograft, allograft, xenograft, demineralized bone, synthetic and natural bone graft substitutes, such as bioceramics and polymers, and osteoinductive factors. A separate carrier to hold materials within the device may also be used. These carriers may include collagen-based carriers, bioceramic materials, such as BIOGLASS®, hydroxyapatite and calcium phosphate compositions. The carrier material may be provided in the form of a sponge, a block, folded sheet, putty, paste, graft material or other suitable form. The osteogenic compositions may include an effective amount of a bone morphogenetic protein (BMP), transforming growth factor $\beta 1$, insulin-like growth factor, platelet-derived growth factor, fibroblast growth factor, LIM mineralization protein (LMP), and combinations thereof or other therapeutic or infection resistant agents, separately or held within a suitable carrier material. Placement may be accomplished directly or with the aid of an injection or transfer device of any effective type.

Embodiments of the implant in whole or in part may be constructed of biocompatible materials of various types. Examples of implant materials include, but are not limited to, non-reinforced polymers, reinforced polymer composites, PEEK and PEEK composites, shape-memory alloys, titanium, titanium alloys, cobalt chrome alloys, stainless steel, ceramics and combinations thereof. Reinforcing materials may include carbon, fiberglass, metal pieces, or any other effective reinforcing material. If a trial instrument or implant is made from radiolucent material, radiographic markers can be located on the trial instrument or implant to provide the ability to monitor and determine radiographically or fluoroscopically the location of the body in the spinal disc space. In some embodiments, the implant or individual components of the implant are constructed of solid sections of bone or other tissues. In other embodiments, the implant is constructed of planks of bone that are assembled into a final configuration. The implant may be constructed of planks of bone that are assembled along horizontal or vertical planes through one or more longitudinal axes of the implant. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof. Examples of resorbable materials that may be used include, but are not limited to, polylactide, polyglycolide, tyrosine-derived polycarbonate, polyanhydride, polyorthoester, polyphosphazene, calcium phosphate, hydroxyapatite, bioactive glass, and combinations thereof. Implant may be solid, porous, spongy, perforated, drilled, and/or open.

FIG. 1 illustrates four vertebrae, $V_1$-$V_4$, of a typical lumbar spine and three spinal discs, $D_1$-$D_3$. While embodiments of the invention may be applied to the lumbar spinal region, embodiments may also be applied to the cervical or thoracic spine or between other skeletal structures.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An expandable medical implant for supporting skeletal structures comprising:
   a base having a first collar, a second collar, a core, a first end positioned at an upper-most portion of the first collar, a second end positioned at a lower-most portion of the second collar, and a cannula extending between the first and second ends along a length of the base, said first collar separate from said second collar and each collar is rotatably connected to said core;
   a first post having a proximal end that travels through the first end of the base and within the cannula and a distal end configured to engage a first vertebrae that extends beyond the first end of the base, the first post includes a first pair of symmetrical legs; and
   a second post having a proximal end that travels through the second end of the base and within the cannula and a distal end configured to engage a second vertebrae that extends beyond the second end of the base, the second post includes a second pair of symmetrical legs;
   wherein the core includes a separator extending across an interior of the base dividing a cross-section of the base into a plurality of wedge sections configured to intervene between all or part of the posts such that the first and second pair of symmetrical legs occupy opposite quarters of the base.

2. The expandable medical implant of claim 1 wherein the base includes the separator dividing the cross-section of the base such that one or more portions of the first post are divided from one or more portions of the second post.

3. The expandable medical implant of claim 2 wherein the separator divides the cross-section substantially into quarters.

4. The expandable medical implant of claim 2 wherein the separator is in close tolerance with the first post and the second post to stabilize the first post and the second post relative to the base.

5. The expandable medical implant of claim 1 wherein the base includes an opening for receiving an actuating instrument.

6. The expandable medical implant of claim 1 wherein the first collar is configured to regulate motion of the first post along the length of the base.

7. The expandable medical implant of claim 6 wherein the first collar is coupled to the first post by threads such that motion of the first post along the length of the base is induced by rotation of the first collar.

8. The expandable medical implant of claim 6 wherein the first collar includes engagement mechanisms around a segment of its interior diameter that allow movement of the first post along the base when the first collar is in a first rotational position and restrict movement of the first post along the base when the first collar is in a second rotational position.

9. The expandable medical implant of claim 6 wherein the first collar includes teeth around its perimeter configured to receive an instrument for rotating the first collar relative to a portion of the base.

10. The expandable medical implant of claim 1 wherein the second collar is configured to regulate motion of the second post along the length of the base.

11. The expandable medical implant of claim 10 wherein the second collar is coupled to the second post by threads such that motion of the second post along the length of the base is induced by rotation of the second collar.

12. The expandable medical implant of claim 10 wherein the second collar includes engagement mechanisms around a segment of its interior diameter that allow movement of the second post along the base when the second collar is in a first rotational position and restrict movement of the second post along the base when the second collar is in a second rotational position.

13. The expandable medical implant of claim 10 wherein the second collar includes teeth around its perimeter configured to receive an instrument for rotating the second collar relative to a portion of the base.

14. The expandable medical implant of claim 1 wherein the first post and the second post each include at least two opposing, interdigitating legs.

15. The expandable medical implant of claim 14 wherein each leg is located substantially at a quarter point of the cross-section of the base.

16. The expandable medical implant of claim 1 wherein the first post is tubular and the second post travels within a passage through the interior of the first post.

17. An expandable medical implant for spacing apart vertebral structures comprising:
   a base having a first collar, a second collar, a core, a first end positioned at an upper-most portion of the first collar, a second end positioned at a lower-most portion of the second collar, and a cannula extending between the first and second ends along a length of the base, said first collar separate from said second collar and each collar is rotatably connected to said core;
   a first post having a proximal end that travels through the first end of the base and within the cannula and a distal end configured to engage a first vertebrae that extends beyond the first end of the base, the first post includes a first pair of symmetrical legs;
   a second post having a proximal end that travels through the second end of the base and within the cannula and a distal end configured to engage a second vertebrae that extends beyond the second end of the base, the second post includes a second pair of symmetrical legs, wherein the core includes a separator extending across an interior of the base dividing a cross-section of the base into a plurality of at least four wedge sections of a circle configured to intervene between the posts such that the first and second pair of symmetrical legs occupy opposite quarters of the base, the separator configured to provide a tolerance of from 0.02 mm to 1 mm between the posts and the separator; and
   an actuating instrument for extending the first post relative to the base and the second post relative to the base in opposite directions in the cannula so that a second height defined by a distance between the distal end of the first post and the distal end of the second post is greater than two times a first height defined by a distance between the distal end of the first post and the distal end of the second post.

* * * * *